United States Patent
McDermott

(10) Patent No.: US 11,376,437 B2
(45) Date of Patent: Jul. 5, 2022

(54) ADJUSTMENT OF THERAPEUTIC STIMULATION

(71) Applicant: DEEP BRAIN STIMULATION TECHNOLOGIES PTY. LTD., East Melbourne (AU)

(72) Inventor: Hugh McDermott, Mount Macedon (AU)

(73) Assignee: DEEP BRAIN STIMULATION TECHNOLOGIES PTY LTD, East Melbourne (AU)

( * ) Notice: Subject to any disclaimer, the term of this patent is extended or adjusted under 35 U.S.C. 154(b) by 703 days.

(21) Appl. No.: 16/481,745

(22) PCT Filed: Jan. 30, 2017

(86) PCT No.: PCT/AU2017/050078
§ 371 (c)(1),
(2) Date: Jul. 29, 2019

(87) PCT Pub. No.: WO2017/127902
PCT Pub. Date: Aug. 3, 2017

(65) Prior Publication Data
US 2019/0388693 A1   Dec. 26, 2019

(30) Foreign Application Priority Data
Jan. 29, 2016  (AU) .............................. 2016900289

(51) Int. Cl.
*A61N 1/36* (2006.01)
*A61N 1/05* (2006.01)
*G05B 13/02* (2006.01)

(52) U.S. Cl.
CPC ........... *A61N 1/36139* (2013.01); *A61N 1/05* (2013.01); *A61N 1/36132* (2013.01); *G05B 13/021* (2013.01)

(58) Field of Classification Search
None
See application file for complete search history.

(56) References Cited

U.S. PATENT DOCUMENTS

| 7,463,927 B1 | 12/2008 | Chaouat |
| 2004/0236389 A1 | 11/2004 | Fink et al. |

(Continued)

FOREIGN PATENT DOCUMENTS

| WO | WO-2004/036377 A2 | 4/2004 |
| WO | WO-2010/044989 A2 | 4/2010 |

(Continued)

OTHER PUBLICATIONS

International Application No. PCT/AU2017/050078, International Search Report and Written Opinion, dated Apr. 20, 2017.

(Continued)

*Primary Examiner* — Brian T Gedeon
(74) *Attorney, Agent, or Firm* — Marshall, Gerstein & Borun LLP

(57) ABSTRACT

Some embodiments relate to a method of adjusting therapeutic stimulation from a therapeutic stimulation system. The method comprising: providing therapeutic stimulation based on a plurality of stimulation parameters to a patient with an implanted controller and at least two electrodes; receiving data indicative of feedback associated with a patient rating of the therapeutic stimulation via a patient input device; automatically adjusting, with the implanted controller, at least one of the plurality of stimulation parameters; and providing adjusted therapeutic stimulation based on the adjusted at least one stimulation parameter to the patient with the controller and the at least two electrodes. The method further comprises receiving additional data indicative of feedback associated with another patient rating of the adjusted therapeutic stimulation; and executing a machine learning algorithm based on the stimulation param- (Continued)

eters and received data indicative of feedback, to determine preferred stimulation parameters.

21 Claims, 6 Drawing Sheets

(56) References Cited

U.S. PATENT DOCUMENTS

| | | | |
|---|---|---|---|
| 2008/0243204 A1* | 10/2008 | Uthman | A61N 1/36071 607/45 |
| 2010/0152813 A1 | 6/2010 | Llneaweaver et al. | |
| 2010/0280334 A1 | 11/2010 | Carlson et al. | |
| 2011/0160796 A1 | 6/2011 | Lane et al. | |
| 2015/0134031 A1 | 5/2015 | Moffitt et al. | |
| 2016/0022995 A1* | 1/2016 | Kothandaraman | A61N 1/36071 607/46 |
| 2016/0096025 A1* | 4/2016 | Moffitt | A61N 1/36139 607/60 |
| 2018/0104500 A1* | 4/2018 | Blum | A61N 1/36132 |

FOREIGN PATENT DOCUMENTS

| | | |
|---|---|---|
| WO | WO-2013/123112 A1 | 8/2013 |
| WO | WO-2015/109239 A1 | 7/2015 |

OTHER PUBLICATIONS

International Application No. PCT/AU2017/050078, International Preliminary Report on Patentability, dated May 18, 2018.
European Patent Application No. 17743504.7, Extended European Search Report, dated Jul. 27, 2020.

* cited by examiner

ADJUSTMENT OF THERAPEUTIC STIMULATION

CROSS-REFERENCE TO RELATED APPLICATIONS

This application is a US National Phase under 35 USC § 371 of International Application No. PCT/AU2017/050078 filed Jan. 30, 2017.

TECHNICAL FIELD

The present disclosure generally relates to processes and systems for adjusting an electronic system that provides therapeutic stimulation to a patient through an implant in the patient.

BACKGROUND

Deep brain stimulation (DBS) is an established therapy for many neurological and psychiatric disorders. DBS systems include a stimulator implanted into the patient (typically within the chest) that is connected to electrodes which are implanted into the brain. A stimulation signal can then be applied by the implanted stimulator to the electrodes which provides a therapeutic effect on the brain. Stimulation parameters can be adjusted using an ex-vivo controller which is an electronic device or computer that is remotely connected to the implanted stimulator.

Although outcomes for most patients presently using DBS are satisfactory, clinicians often have difficulty determining the optimal stimulation parameter settings. The process of optimising the stimulation settings is known as 'fitting'. To achieve the most efficacious therapy while avoiding side-effects, parameters such as stimulation level, pulse width, pulse rate, amplitude modulation and electrode selection need to be chosen individually for each patient during fitting.

The fitting process may be time-consuming and frequently results in suboptimal outcomes. Furthermore, adjustment of the stimulation parameters to maintain efficacious therapy may need to be performed periodically. Adjustment of stimulation parameters may for example be needed several times per year. This may be costly for the patient as a clinician performs the fitting and it may be inconvenient if the patient must travel to a clinic for the fitting.

Any discussion of documents, acts, materials, devices, articles or the like which has been included in the present specification is not to be taken as an admission that any or all of these matters: form part of the prior art base; were common general knowledge in the field relevant to the present disclosure as it existed before the priority date of each claim of this application; or could have been understood, regarded as relevant or reasonably expected to have been combined by a person skilled in the art.

SUMMARY

Some embodiments relate to a method of adjusting therapeutic stimulation from a therapeutic stimulation system. The method comprising: providing therapeutic stimulation to a patient with an implanted controller and at least two electrodes conductively connected to the implanted controller; receiving data indicative of feedback on the efficacy of therapeutic stimulation from the patient via a patient input device; adjusting, with the implanted controller, the therapeutic stimulation; and providing adjusted therapeutic stimulation to the patient with the controller and the at least two electrodes. Advantageously, the implanted controller is capable of providing therapeutic stimulation and adjust the therapeutic stimulation without the need for an ex vivo controller present.

Some embodiments relate to a controller for semi-autonomously adjusting therapeutic stimulation, the controller comprising: a receiver to receive data indicative of feedback from the patient via a patient input device; and a processor configured to: generate a stimulation signal to be applied to the at least two implantable electrodes, and automatically adjust the therapeutic stimulation signal without receiving more data from the patient via the patient input device; and wherein the controller is implantable into a patient, and connectable to at least two implantable electrodes.

Some embodiments relate to a therapeutic stimulation system comprising: a controller according to any one of the embodiments described above; and a patient input device adapted to: receive feedback from the patient; and transmit the data indicative of feedback.

Some embodiments relate to a method of adjusting therapeutic stimulation from a therapeutic stimulation system. The method comprising: providing therapeutic stimulation based on a plurality of stimulation parameters to a patient with an implanted controller and at least two electrodes conductively connected to the implanted controller; receiving data indicative of feedback associated with a patient rating of the efficacy of therapeutic stimulation from the patient via a patient input device; automatically adjusting, with the implanted controller, at least one of the plurality of stimulation parameters, wherein the at least one stimulation parameter is adjusted within a respective limit; and providing adjusted therapeutic stimulation based on the adjusted at least one stimulation parameter to the patient with the controller and the at least two electrodes. The method further comprises receiving additional data indicative of feedback associated with another patient rating of the adjusted therapeutic stimulation from the patient via the patient input device; and executing a machine learning algorithm based on the stimulation parameters and received data indicative of feedback, to determine preferred stimulation parameters. The preferred stimulation parameters may characterise therapeutic stimulation with improved efficacy. Advantageously, the implanted controller is capable of providing therapeutic stimulation and adjust the therapeutic stimulation without the need for an ex vivo controller present.

In some embodiments, the method may comprise: receiving input from the patient at the patient input device, the input indicative of feedback on the efficacy of therapeutic stimulation; and transmitting data indicative of feedback from the patient input device to the implanted controller.

In some embodiments, the method may further comprise receiving the transmitted data indicative of feedback at the implanted controller.

In some embodiments, the therapeutic stimulation may be based on a first set of stimulation parameters, and the adjusting includes adjusting at least one parameter of the first set of stimulation parameters.

In some embodiments, the method may further comprise: receiving feedback from the patient, at the user input device, related to the efficacy of adjusted therapeutic stimulation.

In some embodiments, the steps of: automatically adjusting the therapeutic stimulation, and receiving additional data indicative of feedback from the patient may each be repeated at least once to provide additional input for the machine learning. In some embodiments, the adjusting may be repeated at regular time intervals.

In some embodiments, the automatic adjusting may be based on the received data indicative of feedback from the patient. In some embodiments, the automatic adjusting may include a random adjustment of the at least one stimulation parameter being adjusted.

In some embodiments, the method may further comprise: providing therapeutic stimulation to the patient with the controller and at least two electrodes using the preferred stimulation parameters.

In some embodiments, the adjusting the therapeutic stimulation may include determining, with the controller, a second set of stimulation parameters that characterise a therapeutic stimulation with improved efficacy or to produce a predetermined effect.

In some embodiments, the method may further comprise: providing therapeutic stimulation to the patient with the controller and at least two electrodes using the second set of stimulation parameters.

In some embodiments, the method may further comprise: the controller transmitting data indicating that the controller is receptive to receiving data indicative of feedback; and receiving, at the patient input device, data indicative of the controller being receptive to receiving feedback. In some embodiments, the method may further comprise: indicating, at the patient input device, either a visual or acoustic indication that the controller is receptive to receiving feedback.

In some embodiments, the method may further comprise the implanted controller storing values of the at least one stimulation parameter, and adjusting the at least one stimulation parameter by extrapolating or interpolating from the stored values.

In some embodiments, the method may further comprise the implanted controller storing values of the at least one parameter, and providing therapeutic stimulation based on the preferred set of parameters; wherein the stored parameters are associated with ratings and the preferred set of parameters is associated with a best rating. In some embodiments, the ratings may be numerical and the best rating may comprise a rating with the highest or equal highest numerical value. In some embodiments, the ratings may comprise positive and negative ratings and the best rating may comprise a rating with the most positive ratings.

Some embodiments relate to a controller for semi-autonomously adjusting therapeutic stimulation, the controller comprising: a receiver to receive data indicative of feedback from the patient via a patient input device, wherein the feedback is associated with a patient rating of the therapeutic stimulation; and a processor configured to: generate a stimulation signal based on a plurality of stimulation parameters to be applied to the at least two implantable electrodes, automatically adjust at least one of the plurality of stimulation parameters within a respective limit without receiving more data from the patient via the patient input device; and wherein the controller is implantable into a patient, and connectable to at least two implantable electrodes. The controller is further configured to execute a machine learning algorithm based on the stimulation parameters and received data indicative of feedback, to determine preferred stimulation parameters. The preferred stimulation parameters may characterise therapeutic stimulation with improved efficacy.

In some embodiments, the controller may be further configured to automatically adjust the at least one of the stimulation parameters to improve efficacy of the therapeutic stimulation based on the received data indicative of feedback from the patient.

In some embodiments, the controller further comprises a storage medium capable of storing the plurality of stimulation parameters including the preferred stimulation parameters.

In some embodiments, the controller may further comprise a storage medium capable of storing a first set of stimulation parameters and a second set of stimulation parameters, wherein the generated stimulation signal is based on the first set of stimulation parameters and the therapeutic stimulation signal with improved efficacy or to produce a predetermined effect is based on the second set of stimulation parameters.

In some embodiments, the controller may be configured to adjust at least one parameter of the first set of stimulation parameters when adjusting the therapeutic stimulation signal. In some embodiments, the automatic adjusting of the at least one parameter may be a random change in the at least one parameter.

In some embodiments, the controller may be further configured to repeatedly receive the data indicative of feedback and repeatedly adjust and generate the therapeutic stimulation signal to provide additional input for the machine learning. In some embodiments, the automatic adjusting may be repeated at regular time intervals.

In some embodiments, the controller may further comprise a transmitter to transmit data indicating that the controller is receptive to feedback from the patient.

Some embodiments relate to a therapeutic stimulation system comprising: a controller according to any one of the embodiments described above; and a patient input device adapted to: receive feedback from the patient; and transmit the data indicative of feedback to the controller.

In some embodiments, the evaluating may comprise: receiving input from the patient at the patient input device, the input indicative of feedback on the efficacy of therapeutic stimulation; and transmitting data indicative of the feedback.

In some embodiments, the steps of: adjusting the therapeutic stimulation, and receiving feedback from the patient may each be repeated at least once. In some embodiments, the adjusting may be repeated at regular time intervals.

In some embodiments, the adjusting may be based on the received data indicative of the feedback from the patient. In some embodiments, the adjusting may include a random change in the at least one parameter being adjusted.

In some embodiments, the evaluating may further comprise: the controller transmitting data indicating that the controller is receptive to receiving data indicative of the feedback; and receiving, at the patient input device, data indicative of the controller being receptive to receiving feedback. In some embodiments, the evaluating may further comprise: indicating, at the patient input device, either a visual or acoustic indication that the controller is receptive to receiving feedback.

In some embodiments, the controller may be further configured to adjust the therapeutic stimulation to improve efficacy of the therapeutic stimulation based on the received data indicative of feedback from the patient.

In some embodiments, the controller may be configured to adjust at least one parameter of the first set of stimulation parameters when adjusting the therapeutic stimulation signal. In some embodiments, the adjusting of the at least one parameter may be a random change in the at least one parameter.

In some embodiments, the controller may be further configured to repeatedly receive the data indicative of the feedback and repeatedly adjust and generate the therapeutic stimulation signal. In some embodiments, the adjusting may be repeated at regular time intervals.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments are described in further detail below, by way of example, with reference to the accompanying drawings briefly described below.

DETAILED DESCRIPTION

The present disclosure generally relates to processes and systems for adjusting an electronic system that provides therapeutic stimulation to a patient through an implant in the patient.

More specifically, the embodiments described herein enable an implanted controller to semi-autonomously adjust the therapeutic stimulation provided by the controller without the need for input from a user (such as a clinician) or a device external to the patient to adjust settings that define the therapeutic stimulation. The controller can adjust the therapeutic stimulation and the patient simply provides feedback on the therapeutic stimulation. The controller can determine the settings that lead to the most efficacious therapeutic stimulation.

By allowing the controller to adjust the therapeutic settings, the controller can in some instances automatically and autonomously adjust the therapeutic settings to adjust to certain situations without input from either the patient or a clinician.

Having the controller do the analysis and adjustment also enables a more generic user input device to provide the feedback to the controller.

Figure 1:
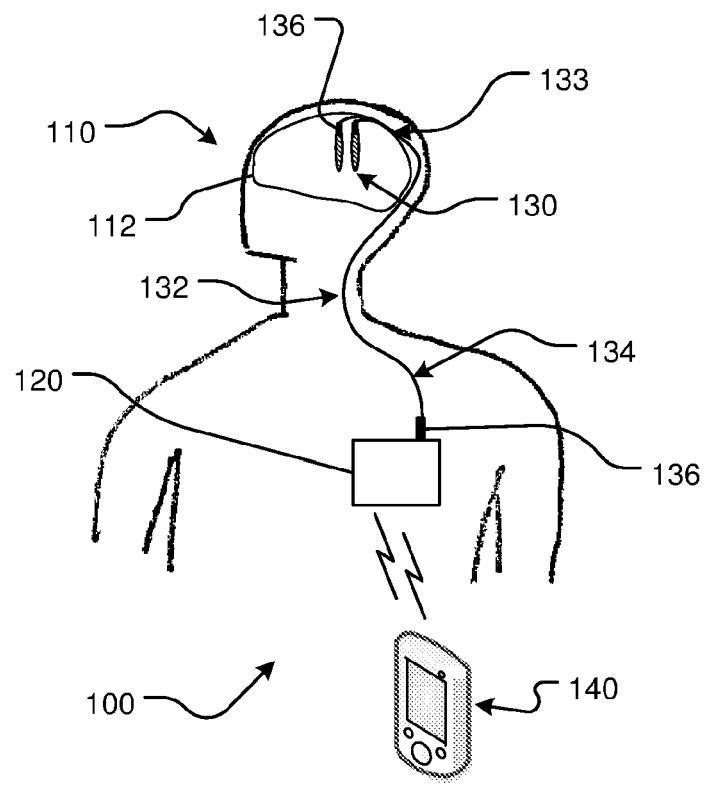
FIG. 1 is a schematic diagram of a therapeutic stimulation system including components implanted into a human patient according to some embodiments.

Referring to FIG. 1, a therapeutic stimulation system 100 is provided. The therapeutic stimulation system 100 comprises a controller 120 and a patient input device 140. The controller 120 is adapted to be implanted into a patient 110, typically in the chest. The controller 120 is also adapted to be electrically conductively connected to at least two electrodes 130 wherein the at least two electrodes 130 are adapted to be implanted into the patient 110 to provide therapeutic stimulation to the patient 110.

Advantageously, the patient input device 140 enables a patient 110 to directly provide feedback on the therapeutic stimulation to the controller 120.

Although FIG. 1 shows the system 100 with respect to patient 110, the patient 110 does not form part of the system 100. However, the therapeutic stimulation system is adapted to be used with a human patient.

Figure 2:
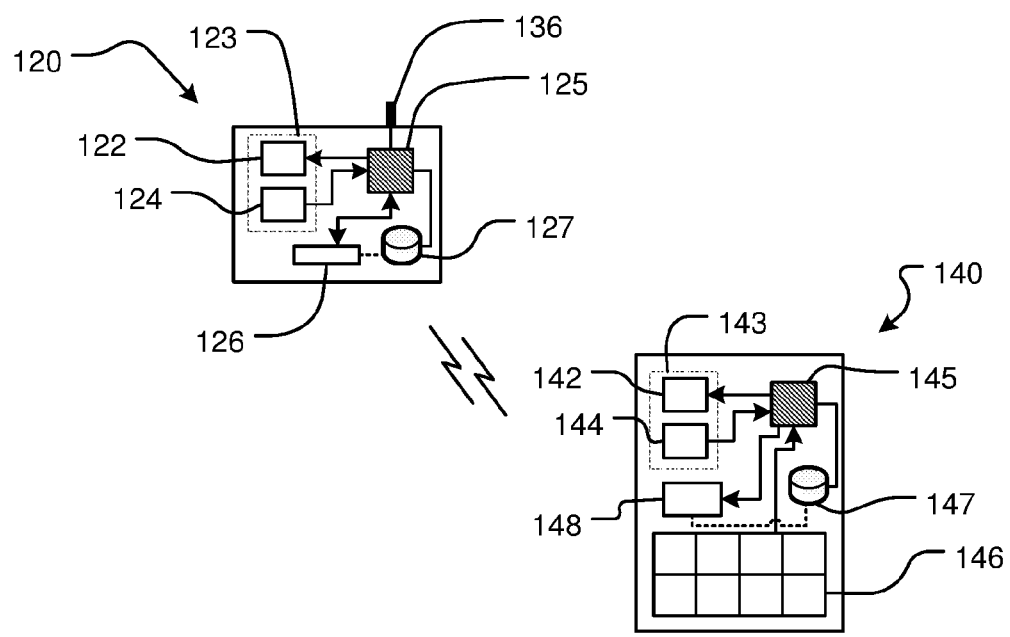
FIG. 2 is a block diagram of a controller and a patient input device according to some embodiments.

Referring to FIG. 2, the controller 120 comprises a first receiver 124 to receive data indicative of the feedback from the patient 110 and, based on the feedback, the controller 120 adapts the therapeutic stimulation to improve efficacy of the therapy or to produce a predetermined effect. The predetermined effect includes avoidance or minimisation of undesirable side-effects of stimulation, or maximisation of battery lifetime (i.e., minimisation of device on-time or stimulation level, which may also be advantageous for safety reasons).

In some embodiments, the controller 120 may also comprise a first transmitter 122 configured to transmit data indicating that the controller 120 is receptive to receiving feedback from the patient 110. This can be used, for example, to prompt the patient 110 to provide feedback with the patient input device 140. In some embodiments, the first transmitter 122 and first receiver 124 are co-located or integral to a first transceiver 123.

In some embodiments, the controller 120 may also be configured to transmit data that includes details on stimulation parameters 152 that characterise the therapeutic stimulation being provided to the patient 110.

Figure 3A:
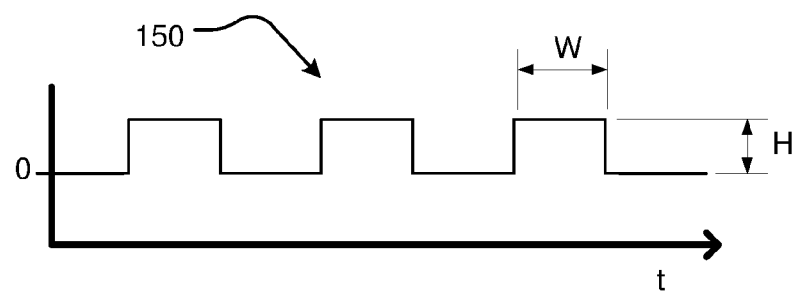
FIG. 3A is a plot of a therapeutic stimulation signal according to some embodiments.
Figure 3B:
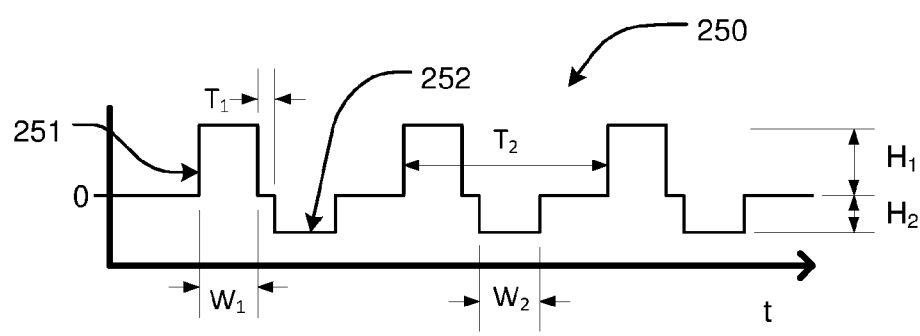
FIG. 3B is a plot of a therapeutic stimulation signal according to some embodiments.
Figure 3C:
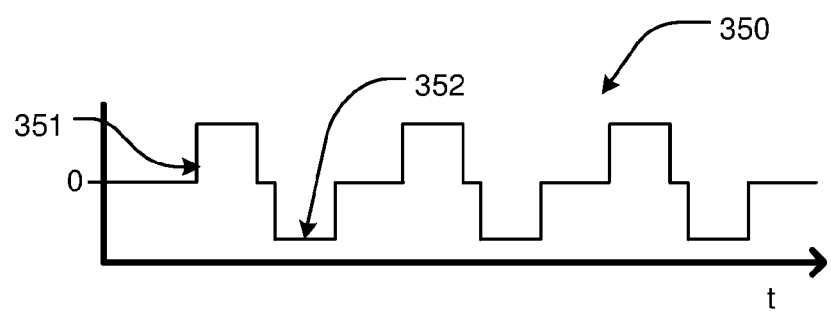
FIG. 3C is a plot of a therapeutic stimulation signal according to some embodiments.

The controller 120 may further comprise a processor 125, a storage medium 126 and a power source 127. The processor 125 is configured to generate a stimulation signal 150 (examples of this are shown in FIGS. 3A-3C) and adjust the therapeutic stimulation. The therapeutic stimulation provided by the controller 120 to the electrodes 130 may be based on a set of stimulation parameters 152 that may be stored in the storage medium 126 which is machine readable. The set of stimulation parameters 152 may include a plurality of stimulation parameters. The power source 127 is connected to the processor 125 and may be connected to the storage medium 126 to provide power to the processor 125 and the storage medium 126.

In some embodiments, controller 120 may further comprise a separate signal generator and timing circuitry that interact with processor 125 to generate the stimulation signal 150.

In some embodiments, the storage medium 126 for storing the stimulation parameters may comprise one or a series of: memory registers, non-volatile memory such as flash memory, or Electrically Erasable Programmable Read-Only Memory (EEPROM). The controller 120 may be considered to comprise a computing device. The computing device comprises the processor 125 and the storage medium 126 and the power source 127. The processor 125 is configured to read and execute machine readable instructions stored on the storage medium 126. The machine readable instructions may be based on code or algorithms that, when executed by the processor 125, can use the controller to execute any of the methods 600, 800 described below.

The patient input device 140 comprises a second transmitter 142 and a user interface 146. The second transmitter 142 is adapted to transmit data indicative of feedback from the patient 110. The user interface 146 is adapted to receive input indicative of feedback from the patient 110.

In some embodiments, the user interface 146 may include a keypad, a touch screen, a microphone, one or more buttons or one or more switches.

Feedback from the patient 110 is intended to include direct feedback from the patient and indirect feedback from the patient 110 via another person. For example, the patient 110 may communicate feedback to a carer, clinician or another person who may provide input indicative of feedback into the patient input device 140 on behalf of the patient 110.

The patient input device 140 may include a processor 145, a power source 147 and a display 148. The processor 145 is used to control the inputs from the user interface 146 and the output to the second transmitter 142. The power source 147 is connected to the processor 145 and may also be connected to the display 148 to provide power to the processor 145 and the display 148.

In some embodiments, the patient input device 140 optionally includes a second receiver 144. The second receiver 144 is adapted to receive the indication that the controller 120 is receptive to feedback and transmit this to the processor 145. In some embodiments, the second transmitter 142 and the second receiver 144 are co-located or integral to a second transceiver 143.

The processor 145 may also send data to display 148 in response to receiving data indicating that the controller 120 is receptive to feedback and to visually indicate that the controller 120 is receptive to feedback from the patient 110. In some embodiments, processor 145 may send a signal to an audio output or vibration component to indicate that the controller 120 is receptive to feedback.

In some embodiments, the patient input device 140 may be embodied within an electronic user device such as a smart phone, a tablet computer, a laptop computer or a desktop computer.

As shown in FIG. 1, there may be at least two electrodes 130 implanted into the brain 112 of the patient 110. For example, at least one electrode 130 may be implanted into each hemisphere of the brain 112. Each electrode 130 is adapted to be electrically connected to one end 133 of an electrical lead 132 and the opposite end 134 of the electrical lead 132 is adapted to be connected to the processor 125 by connections 136. In some embodiments, at least one electrode 130*a* is implanted into the brain 112 and at least one electrode 130*b* is implanted into the patient 110 at a location other than the brain 112. In some embodiments, at least one electrode 130*b* may be attached to an external surface of the implanted controller 120.

In some embodiments, any one of the connections 136 between the electrical lead 132 and the processor 125, or the connections between the electrical lead 132 and the electrode 130, may be connected such that the connection 136 resists being electrically conductively disconnected when implanted in the patient 110. In some embodiments, the connection 136 may include a clamp, or a socket and a plug. In some embodiments, the connection 136 may be a fixed connection comprising a solder joint or weld.

The stimulation signal 150 provided by the controller 120 is used to provide an electrical output from the at least two electrodes 130 to thereby provide therapeutic stimulation.

Referring to FIG. 3A, the stimulation signal 150 may be a repetitive signal based on stimulation parameters 152 which includes any one or more of: a frequency f, pulse modulation type, pulse height H and pulse width W. The pulse modulation type may for example be a square wave. The pulse height H may be related to an electrical current provided to the electrode 130 or a voltage provided to the electrode 130.

Referring to FIG. 3B, the stimulation signal 250 may comprise a repetitive signal comprising two or more square wave pulses. A first square wave pulse 251 may be characterised by first pulse height $H_1$ and first pulse width $W_1$. A second square wave pulse 252 may be characterised by a second pulse height $H_2$ and a second pulse width $W_2$. The start of the second square wave pulse 252 may occur at a time $T_1$ after the end of the first square wave pulse 251. The period between successive pulses may be characterised by a time $T_2$. The sum of the pulse widths $W_1$, $W_2$ and the period between the square wave pulses $T_1$ is less than or equal to the period between successive pulses $T_2$.

In some embodiments, the second square wave pulse 252 may have a negative electrical polarity relative to the first square wave pulse 251. In some embodiments, the second pulse width $W_2$ may be larger than the first pulse width $W_1$. In some embodiments, the first pulse height $H_1$ may be larger than the second pulse height $H_2$.

Referring to FIG. 3C, stimulation signal 350 is shown as a special case of stimulation signal 250 where the first square wave pulse 351 and second square wave pulses 352 have a pulse height $H_1$ and pulse height $H_2$ that are equal.

In some embodiments, the period between the square wave pulses $T_1$ may be zero.

In some embodiments, at least one of the stimulation parameters 152 is fixed and set by a clinician. The at least one fixed stimulation parameter cannot be varied by the controller 120 or the patient 110 without the involvement of the clinician. In some embodiments this feature may be provided for by configuring the processor 125 to only allow the fixed parameter to be adjusted if a specific passkey or password is entered into the patient input device 140. Alternatively, the clinician may use a clinician input device separate from the patient input device 140 which communicates directly with the implanted controller 120 to set the parameters 152 including the at least one fixed stimulation parameter.

The clinician may also set an upper or lower limit to any one of the stimulation parameters 152 to ensure that the system and/or patient do not adjust the stimulation parameters 152 such that an unsafe or uncomfortable electrical output is produced at the electrode 130. The limits could be set during an initial fitting session to establish respective limits that may be fixed limits for each parameter 152 or a combination of parameters 152. Each stimulation parameter may have a different limit. The controller would be prevented from generating a therapeutic signal using parameters outside those limits.

In some embodiments, the controller 120 is adapted to receive information about other relevant conditions that are expected to vary over time. The patient input device 140 may include an appropriate user interface to enable the patient to input information relating to these conditions. These conditions may include usage of medications and patient state (e.g., type of physical or mental activity the patient is performing or experiencing). In some embodiments, the relevant condition may include the anatomical locations of the electrodes. Accordingly, the controller 120 can, when adjusting the therapeutic stimulation, take into account these conditions. For example, the therapeutic stimulation may automatically change when an indication that medication has been taken is received by the controller 120.

The controller 120 may also be configured to receive signals from brain activity (e.g., local field potentials recorded from implanted electrodes 130). Characteristics of these signals may be taken into account when adjusting the therapeutic stimulation.

In some embodiments, the controller 120 may include an internal clock. The internal clock may be internal to or separate from the processor 125 and enables the controller 120 to take into account relevant coincident objective measures, such as time of day (or longer time periods). For example, the controller 120 may adjust or turn off the therapeutic stimulation after a duration of continuous stimulation or after certain time of day such as when it is likely the patient is sleeping.

Figure 4:
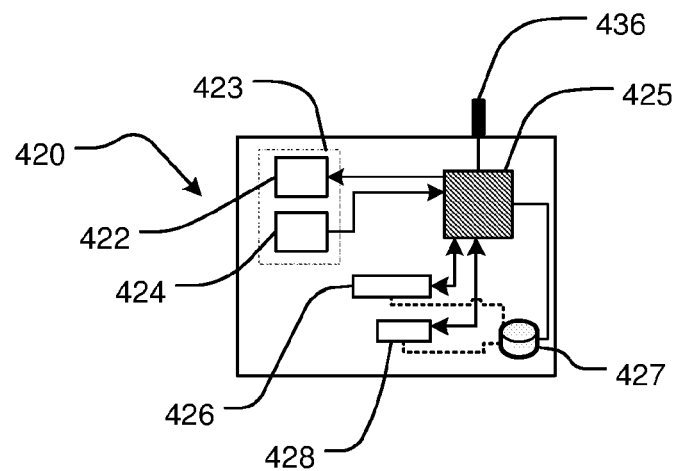
FIG. 4 is a block diagram of a controller according to some embodiments.

Referring to FIG. 4, in some embodiments, the system 100 may include implantable controller 420. The implantable controller 420 may be identical to controller 120 and comprise a receiver 424, a processor 425, a storage medium 426 and a power source 427. The power source 427 is connected to the processor 425 and may be connected to the storage medium 426 to provide power to the processor 425 and the storage medium 426. The controller 420 further comprises an electrical connection 436 to enable the processor 425 to be connected to implantable electrodes and provide therapeutic stimulation. In some embodiments, the controller 420 further comprises a first transmitter 422 and first receiver 424. In some embodiments, the first transmitter 422 and first receiver 424 are co-located or integral to a first transceiver 423.

Implantable controller 420 further comprises at least one sensor 428. For example, sensor 428 may comprise any one of: a movement sensor, a temperature sensor and an orientation sensor. The controller 420 may be adapted to receive data from the movement sensor to adjust the therapeutic stimulation. For example, if a movement sensor, a location sensor, and/or an orientation sensor provide data indicating that the patient 110 is sleeping, the therapeutic stimulation may be automatically adjusted to a therapeutic stimulation signal appropriate for a sleeping patient 110. For example, the therapeutic stimulation signal may be reduced in intensity or switched off. In some embodiments, an orientation sensor can be used to determine if the patient 110 is lying in a supine or prone position.

Figure 5:
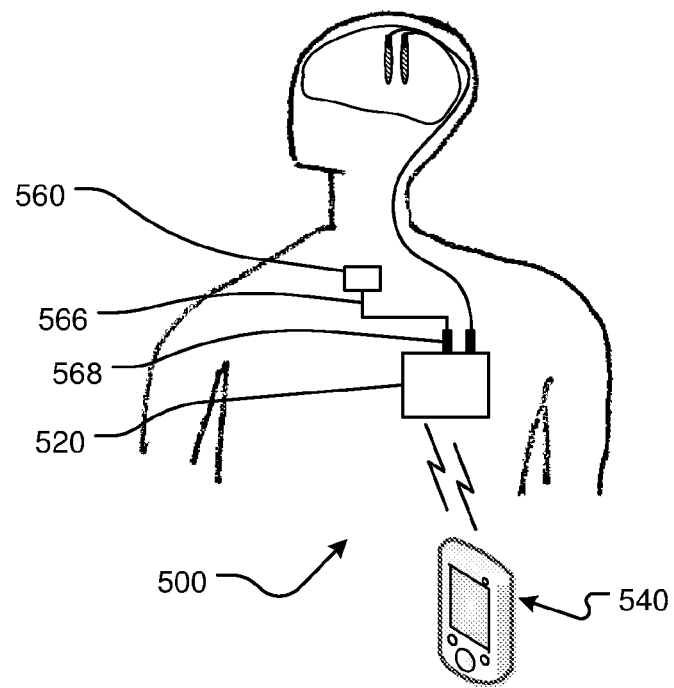
FIG. 5 is a schematic diagram of a therapeutic stimulation system including components implanted into a human patient according to some embodiments.

Referring to FIG. 5, there is provided a therapeutic stimulation system 500 according to some embodiments. Therapeutic stimulation system 500 may be identical to therapeutic stimulation system 100 but also include at least one sensor 560 which is connected to the controller 520. The sensor 560 may be electrically conductively connected to the controller 520 or wirelessly connected. The sensor 560 may be implanted within the body or it may be external to the body (such as a wearable sensor). In some embodiments, sensor 560 is electrically conductively connected to processor 525 at an electrical connection 568. Controller 520 is adapted to receive data from the at least one implanted sensor 560. Connection 568 may be identical or similar to connection 136 in system 100. In embodiments where the sensor 560 is connected wirelessly to controller 520, sensor 560 includes a transmitter 562 and may include a receiver 564 for communicating with the controller 520.

In some embodiments, the sensor 560 comprises any one of a movement sensor, a temperature sensor, a position sensor, a location sensor, an orientation sensor, a microphone and an acoustic sensor (which may be used for indicating vocal properties of the user). The controller 520 can use data from the at least one implanted sensor 560 to adjust the therapeutic stimulation.

Advantageously, by associating feedback from the patient with some or all of the data provided from any one or more of the movement sensor, microphone, acoustic sensor or clock, the controller 120, 420, 520 of system 100, 500 may more efficiently or more quickly converge on stimulation parameters 152 that are closer to the optimum parameters for providing high efficacy therapy or a predetermined effect in comparison with the use of patient feedback alone.

Figure 6:
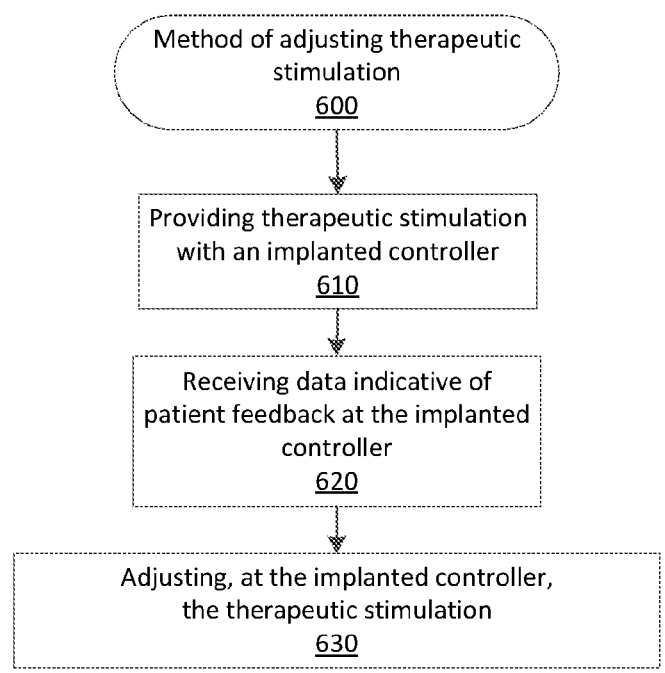
FIG. 6 is a flow diagram of a method of adjusting therapeutic stimulation according to some embodiments.

Referring to FIG. 6, there is also provided a method of adjusting therapeutic stimulation 600 using a therapeutic stimulation system 100, 500. The method comprises providing therapeutic stimulation to the patient 110 with the controller 120, 420, 520 and at least two electrodes, at 610. The method further comprises the implanted controller 120, 420, 520 receiving data indicative of feedback, at 620, and adjusting, at the implanted controller, the therapeutic stimulation, at 630. The adjusting may comprise adjusting at least one of the stimulation parameters 152. The system 100, 500 thereby semi-autonomously adjusts the therapeutic stimulation provided by the controller 120, 420, 520 and allows the patient 110 to evaluate the therapeutic stimulation and provide feedback to the controller 120, 420, 520. In some embodiments, the data indicative of feedback can then be stored and associated with the stimulation parameters that the therapeutic stimulation provided was based on.

In some embodiments, the method 600 is repeated indefinitely. In some embodiments, the method 600 is repeated at regular time intervals The time intervals may, for example, be less than 5 minutes, or in the range of: 1 to 10 minutes, 1 to 5 minutes, 5 to 30 minutes, 10 to 20 minutes, 0.5 to 3 hours, 1 to 2 hours, 1 to 31 days, or 1 to 7 days. As the patient input device 140 allows input from the patient 110, the patient 110 advantageously need not be present at a medical clinic or hospital for method 600 to be performed.

Figure 7:
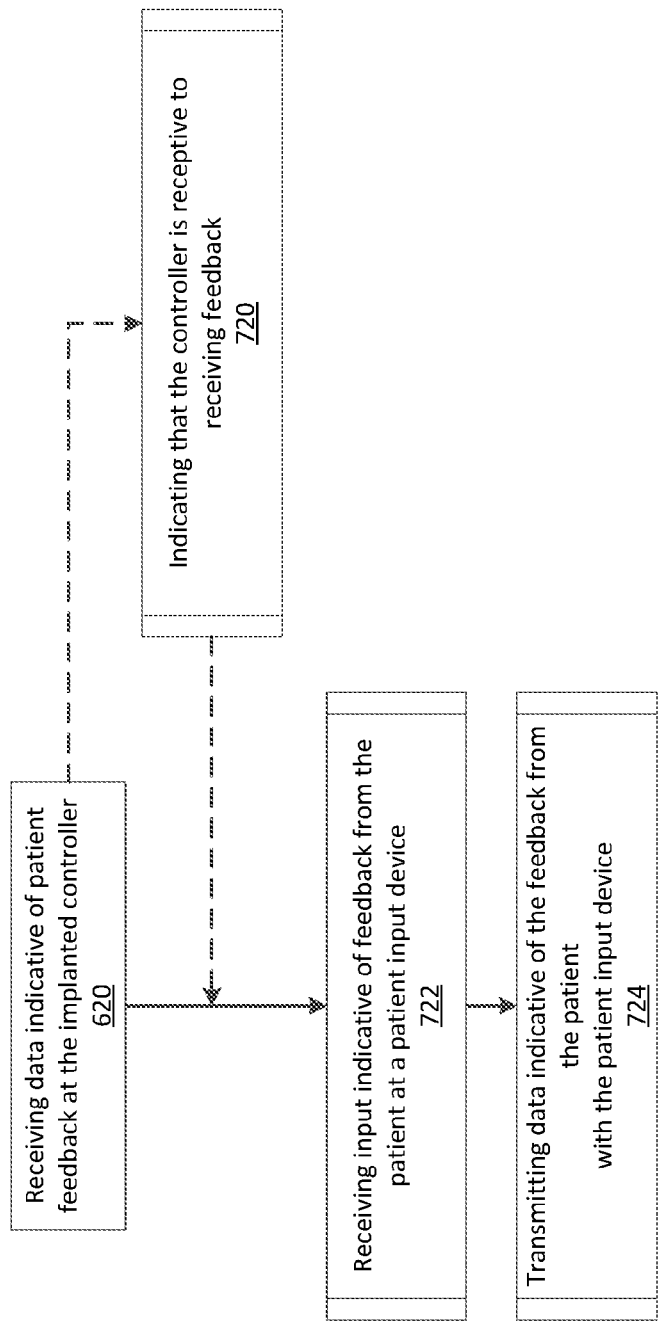
FIG. 7 is a flow diagram for receiving patient feedback at an implanted controller according to some embodiments.

Referring to FIG. 7, according to some embodiments the step of receiving data indicative of patient feedback 620 may include:

receiving input, at a patient input device 140, wherein the input is indicative of feedback on the efficacy of therapeutic stimulation from the patient 110 or level of side effects experienced by the patient 110, at 722; and transmitting data indicative of feedback, by the patient input device 140, at 724.

The transmitting of data 724 may include transmitting from the patient input device 140 to the implanted controller 120, 420, 520. The method 600 may comprise the implanted controller 120, 420, 520 receiving the transmitted data.

In some embodiments, the received patient input that is indicative of the efficacy of the therapeutic stimulation from the patient 110 at 620 may be associated with and/or take the form of a rating of the efficacy of the therapeutic stimulation being provided to the patient 110. The rating may be selected from a discrete set of qualitative alternatives which may be presented on the display of the patient input device. For example, in some embodiments, the patient input device may display alternatives such as very poor, poor, OK, good, very good or excellent. In some embodiments, the rating may be a single indication of either a good or bad experience of the stimulation by the patient 110. This could be indicated by input into the user interface 146 via a single button. In some embodiments, the alternatives for the ratings may be numerical and the feedback may, for example, be in the form of a number between 1 and 10 (including 1 or 10).

In some embodiments, the feedback may include an indication of the incidence of any side-effects experienced by the patient 110.

In some embodiments, the feedback may include indications of more than one relevant effect. In these embodiments, the user interface 146 of the patient input device 140 may include multiple user-actuable controls for indicating the rating for each of the relevant effects. The controls may comprise variable electrical switches each comprising a protrusion such as a knob or handle. Alternatively, the controls may be displayed as 'virtual' controls on a touch screen to mimic variable analogue electrical switches. In some embodiments, the ratings for each relevant effect may be either a selection of a qualitative alternative, a pictographic illustration (such as an emoji or emoticon) or a numerical rating as described above. The pictographic illustration could for example represent a smiley face, sad face, thumbs up or thumbs down.

In some embodiments, the step of receiving data indicative of patient feedback 620 may optionally comprise the step of indicating that the controller 120, 420 is receptive to receiving feedback, at 720. This can, for example, comprise the patient input device 140 prompting the patient 110 to provide feedback with the patient input device 140. In some embodiments, indicating 720 may include transmitting an indication (such as a signal or data) that the controller 120, 420 is receptive to receiving feedback from the controller 120, 420 and receiving the indication at the patient input device 140.

The step of receiving data indicative of patient feedback at 620 may also use the system 500.

After receiving data indicative of patient feedback at 620 the controller 120, 420, 520 then adjusts the therapeutic stimulation at 630 and may provide the adjusted therapeutic stimulation to the patient 110 at 640. The adjustment 630 of the therapeutic stimulation comprises changing any one or more of the stimulation parameters 152 that define the therapeutic stimulation; i.e. any one or more of the selected active electrode(s), frequency f, pulse modulation type, pulse height H and pulse width W could be changed. The changing may involve incrementing or decrementing one or more stimulation parameters by a set amount, for example. How the parameters can be changed will be discussed in further detail below.

The adjustment 630 and provision of the adjusted therapeutic stimulation 640 step are conducted automatically and autonomously by the controller 120.

In some embodiments, the step of adjusting the therapeutic stimulation 630 may include adjusting a single parameter of the set of parameters 152. The adjusted set of parameters 152 may be stored on the storage medium 126, 426. The ratings could therefore refer to the patient's experience of a single parameter setting. In other embodiments, the feedback could be a comparison of the patient's experience of two or more settings which are being varied in the adjustment of the therapeutic stimulation 630.

In some embodiments, the adjustment may be a random adjustment of the stimulation parameters 152. Advantageously, the random adjustment of stimulation parameters avoids any confirmation bias introduced by a progressive variation in a particular parameter.

In some embodiments, the stimulation parameters 152 may be stored on the storage medium 126, 426 and the adjustment 630 may change the stimulation parameters 152 based on the previously stored stimulation parameters. For example, the adjustment 630 may avoid generation of an adjusted therapeutic stimulation defined by previously stored stimulation parameters. This prevents repetition of the same therapeutic stimulation signal.

In some embodiments, the adjustment 630 may be based on the received data indicative of the feedback from the patient. However, the feedback may not specifically prescribe how the adjustment 630 is to be implemented or what the adjusted therapeutic stimulation signal is.

In some embodiments, the processor 125, 425 may execute an algorithm stored on the storage medium 126, 426 such as a machine learning algorithm to adjust the stimulation parameters 152 and therefore the therapeutic stimulation. The machine learning algorithm may use the stored stimulation parameters and analyse feedback associated with the stored stimulation parameters to adjust the stimulation parameters 152. The machine learning algorithm may therefore be based on the stimulation parameters 152 and the received data indicative of feedback.

In some embodiments, the machine learning algorithm may extrapolate or interpolate stimulation parameters to enable the controller 120 to generate therapeutic stimulation with increased efficacy or any other desired outcome depending on the nature of the feedback provided. The machine learning algorithm may thereby determine preferred stimulation parameters that characterize therapeutic stimulation with improved efficacy.

In an example of parameter extrapolation, if an increase in the value of one stimulation parameter defining the therapeutic stimulation signal leads to positive feedback (such as in the form of an increasing rating by the patient); then the processor 125 may adjust the parameter by further increasing the value of the parameter.

In an example of parameter interpolation, if a decrease in the value of a stimulation parameter previously led to a positive rating but a continued decrease in the stimulation parameter now results in a negative rating, then the processor 125 may adjust the parameter by next increasing the value of the parameter to a value that is in between the previous two values.

In an example of changing the type of therapeutic stimulation signal generated, the processor 125 executing a machine learning algorithm for adjusting the signal may simply cycle through the available types of stimulation signals, receive data indicative of feedback and store an association of the feedback for each type. Once feedback has been received for all types, the processor 125 executing a machine learning algorithm may change the type of stimulation signal to the type that is associated with the most positive feedback. In the event that two types have the same level of positive feedback, the processor 120 may be programmed to either randomly select one of the types or prompt the patient 110 to choose one by displaying a question on the display 148 of the patient input device 140, 540.

After the adjustment of the therapeutic stimulation 630, the patient 110 then evaluates the adjusted therapeutic stimulation, and the controller further adjusts and provides therapeutic stimulation. The process of evaluating the adjusted therapeutic stimulation 645 may be the same as the process of the patient evaluating the therapeutic stimulation 620 and may comprise receiving additional data indicative of feedback.

Method 600 may provide additional input, for example in the form of stimulation parameters and data indicative of feedback, for machine learning.

Figure 8:
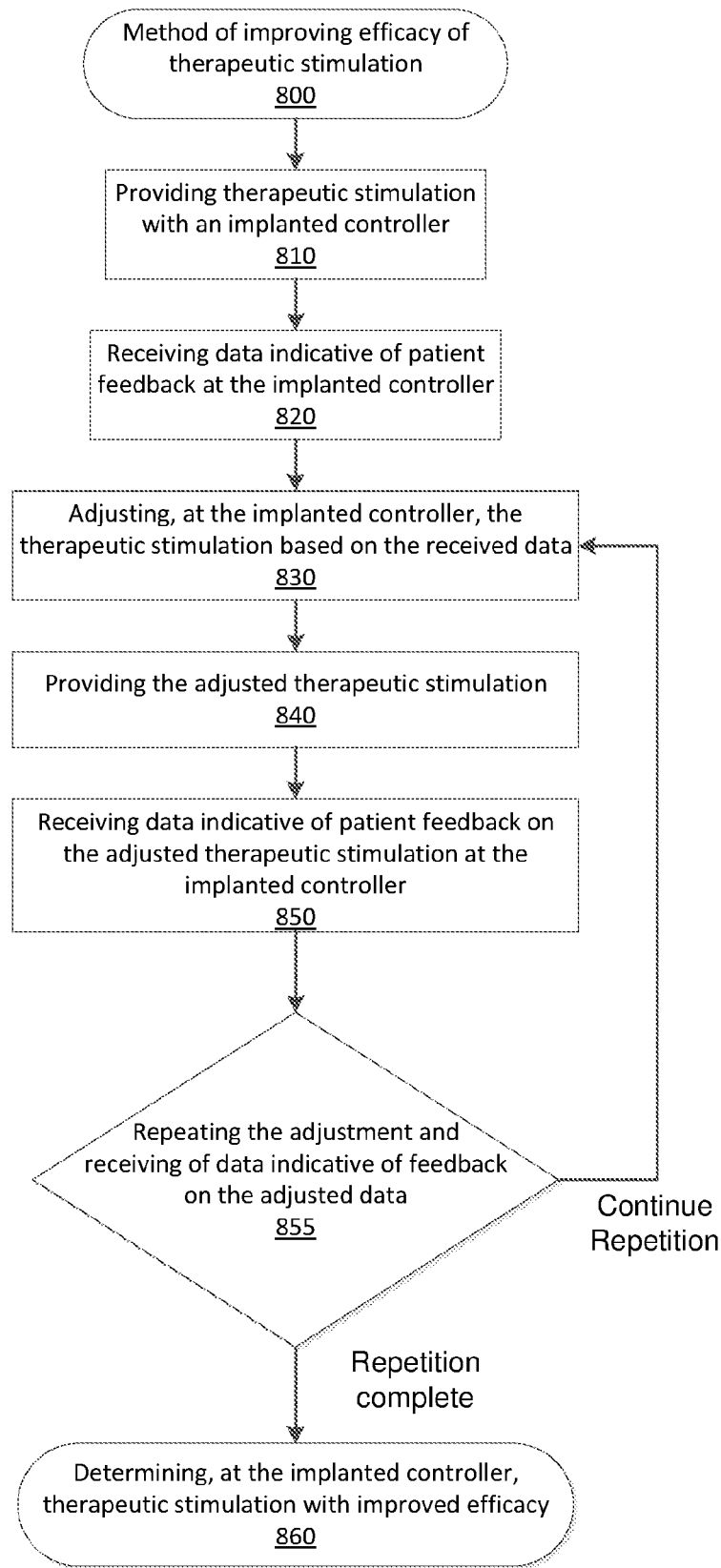
FIG. 8 is a flow diagram of a method of improving efficacy of therapeutic stimulation according to some embodiments.

Referring to FIG. 8, a method 800 of improving efficacy of therapeutic stimulation is shown and described in further detail below.

Method 800 of improving efficacy of therapeutic stimulation comprises: providing therapeutic stimulation with an implanted controller, at 810; receiving data indicative of patient feedback at the implanted controller, at 820; adjusting, at the implanted controller, the therapeutic stimulation based on the received data 830. These steps are in common to method 600 and the step of receiving data indicative of patient feedback at the implanted controller, at 820 may be identical to step 620 described above. However, method 800 further comprises providing the adjusted therapeutic stimulation, at 840 and receiving data indicative of patient feedback on the adjusted therapeutic stimulation at the implanted controller 120, 420, 520, at 850. The steps of adjusting the therapeutic stimulation 840 and receiving data indicative of patient feedback on the adjusted therapeutic stimulation 850 are then repeated, at step 855. The method further comprising determining, at the implanted controller, therapeutic stimulation with improved efficacy 860. The implanted controller 120, 420, 520 thereby uses method 800 to optimise or improve the efficacy of the therapeutic stimulation provided.

In some embodiments, the method 800 may further include storing the data indicative of feedback and storing an association with the set of therapeutic stimulation parameters that the therapeutic stimulation was based on immediately before or at the time of the patient's input.

In some embodiments, the step of repeating 855 is repeated a fixed number of times before the step of determining 860 therapeutic stimulation with improved efficacy. In other embodiments, the step of repeating 855 is repeated at regular time intervals using the internal clock of the controller 120, 420, 520. The time intervals may, for example, be less than 5 minutes, or in the range of: 1 to 10 minutes, 1 to 5 minutes, 5 to 30 minutes, 10 to 20 minutes, 0.5 to 3 hours, 1 to 2 hours, 1 to 31 days, or 1 to 7 days.

In some embodiments, the method 800 is repeated indefinitely. In some embodiments, the method 800 is repeated at regular time intervals using the internal clock of the controller 120, 420, 520. The second time interval over which method 800 is repeated is larger than the first time interval for repeating the step 855. In some embodiments, the second time interval is at least twice the first time interval. The time intervals may, for example, be less than 5 minutes, or in the range of: 1 to 10 minutes, 1 to 5 minutes, 5 to 30 minutes, 10 to 20 minutes, 0.5 to 3 hours, 1 to 2 hours, 1 to 31 days, or 1 to 7 days.

The controller 120 can be used to semi-autonomously calculate efficacious stimulation parameters by analysing the data indicative of feedback from the patient. This may be achieved with the processor 125, 425 using any known machine learning or fuzzy-logic algorithms for optimising stimulation parameters.

By analysing the pattern of patient feedback inputs in relation to the stimulation parameters, the therapeutic system 100, 500 'learns' an optimal setting of stimulation parameters for that patient 110. There are many established techniques for automatic learning that might be applicable to the controller 120, 420, 520. For instance, the controller 120, 420, 520 could count the number of positive patient feedback inputs (or 'votes') for each setting, and after an acceptable predetermined number of votes have been accumulated for any one of the settings, the controller 120, 420, 520 could automatically apply the patient's most-preferred setting. For example, at least 2 votes for a particular setting could be predetermined as the acceptable number of votes for a most-preferred setting. In some embodiments, the predetermined number of votes may be 5 to 10 votes for a most-preferred setting. In some embodiments, more than 10 votes may be required for a most-preferred setting.

In some embodiments, the automatic application of the setting with the highest number of votes occurs after a predetermined total number of votes across all settings has been received by the controller 120, 420, 520. In some embodiments, the predetermined total number of votes may be 25 to 75 or more, for example 50 total votes may be required.

In some embodiments, a more complex and potentially more effective learning technique may be used, comprising automatically changing the therapeutic stimulation in response to the pattern of data indicative of feedback and then gathering additional feedback on the adjusted therapeutic stimulation. In this way, the controller 120, 420, 520 would automatically converge towards an optimal setting of stimulation parameters over time, even if that setting had not been presented to the patient previously by way of a therapeutic stimulation signal based on such a setting.

In some embodiments, the controller 120, 520 transmits data to the patient input device 140, 540 to prompt the patient 110 to compare two alternative therapeutic stimulations based on different sets of stimulation parameters 152 and provide feedback on the preferred stimulation. When therapeutic stimulation based on a particular set of parameters has accumulated enough positive feedback, these parameters can be retained as reference parameters 153 to provide a reference stimulation as a basis for comparison. The therapeutic stimulation parameters 152 can then be changed to an alternative set of stimulation parameters 154. The patient 110 would then be prompted to compare the stimulation based on the alternative parameters 154 with the retained set of reference parameters 153. If this process is repeated multiple times, the processor 125, 425, 525 may use an evolutionary algorithm to then determine optimal or preferred therapeutic stimulation parameters 152. One example of a similar scheme is known as a 'genetic' algorithm. With such algorithms, parameters 152 may initially be randomly chosen but with further iterations those with poor feedback (such as low ratings) are dismissed whereas those with good feedback (such as higher ratings) are used as the basis for generating the adjusted therapeutic stimulation. In this way the therapeutic stimulation is adapted in a similar way to natural selection in evolutionary theory and the 'fittest' therapeutic stimulation parameters survive.

In some embodiments, at least one of the therapeutic parameters is randomly changed to provide a random change in the therapeutic parameter. Over time, this scheme would apply a wide range of settings by random sampling and obtain user preference data for each of them. In common with the other learning schemes already mentioned, this would eventually converge on an overall preferred setting for that user.

In some embodiments, the adjustment may be conducted at scheduled time intervals, at randomly selected times, or over regular time intervals. In such embodiments, there may not be an indication (such as a visual or audio indication) on the patient input device 140 that the controller 120 is receptive to feedback from the patient 110. However, in some embodiments, the patient input device 140 may be configured to prompt the patient to provide feedback. This may occur without the need for the implanted controller 120 indicating that it is receptive to feedback. The intervals between adjustments may, for example, be less than 5 minutes, or in the range of: 1 to 10 minutes, 1 to 5 minutes, 5 to 30 minutes, 10 to 20 minutes, 0.5 to 3 hours, 1 to 2 hours, 1 to 31 days, or 1 to 7 days.

In some embodiments, the storage medium 126 is used to store a machine learning algorithm used by the processor 125 to implement the method 600 or 800. In some embodiments, the learning algorithm could be programmed with an intentional bias to achieve certain benefits. For example, there may be a patient preference weighted towards therapeutic stimulation that is likely to maximise battery lifetime, minimise side-effects, or minimise application of stimulation that may be judged less safe (e.g., a combination of high levels and high rates on multiple electrodes). In an illustrative instance, if therapeutic stimulation based on two different sets of therapeutic stimulation parameters have received approximately the same ratings from the user, the stimulation parameters that define the therapeutic stimulation requiring less battery power or lower levels of stimulation would be automatically applied by the implanted controller 120, 420, 520.

Although the above embodiments describe methods and systems for adjusting and optimisation of settings for Deep Brain Stimulation (DBS), the same principles could be applied to other forms of stimulation, such as transcranial direct- or alternating-current stimulation, transcranial magnetic stimulation, ultrasonic stimulation, and mechanical delivery of medications.

In embodiments where magnetic stimulation or ultrasonic stimulation is delivered, settings may include parameters relating to periodic or pulsed signals such as stimulation level, pulse width, pulse rate and amplitude modulation. Additionally, implanted electrodes may not be needed for magnetic stimulation or ultrasonic stimulation and electrode coils may be placed external to the skull to stimulate neurons in the patient's brain.

In some embodiments, combinations of therapy could be controlled by embodiments of the controller 120, 520. For example, combinations of DBS and drugs could be rated by the user and settings of the drug-delivery parameters (such as dosing frequency or strength) could be optimised automatically at the same time as the DBS settings.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of adjusting therapeutic stimulation from a therapeutic stimulation system, the method comprising:
   providing therapeutic stimulation based on a plurality of stimulation parameters to a patient with an implanted controller and at least two electrodes conductively connected to the implanted controller;
   receiving data indicative of feedback associated with a patient rating of the therapeutic stimulation from the patient via a patient input device;
   automatically adjusting, with the implanted controller, at least one of the plurality of stimulation parameters without receiving more data from the patient via the patient input device, wherein the at least one stimulation parameter is adjusted within a respective limit and the automatic adjusting includes a random adjustment of the at least one stimulation parameter being adjusted;
   providing adjusted therapeutic stimulation based on the adjusted at least one stimulation parameter to the patient with the controller and the at least two electrodes;
   receiving additional data indicative of feedback associated with another patient rating of the adjusted therapeutic stimulation from the patient via the patient input device; and
   executing a machine learning algorithm based on the stimulation parameters and received data indicative of feedback, to determine preferred stimulation parameters.

2. The method of claim 1, further comprising:
   receiving input from the patient at the patient input device, the input indicative of feedback on the therapeutic stimulation; and
   transmitting data indicative of feedback from the patient input device to the implanted controller.

3. The method of claim 2, further comprising:
   receiving the transmitted data indicative of feedback at the implanted controller.

4. The method of claim 1, wherein the steps of:
   automatically adjusting the therapeutic stimulation, and
   receiving additional data indicative of feedback from the patient are each repeated at least once to provide additional input for the machine learning.

5. The method of claim 4, wherein the automatic adjusting is repeated at regular time intervals.

6. The method of claim 1, wherein the automatic adjusting is based on the received data indicative of feedback from the patient.

7. The method of claim 1, further comprising:
   providing therapeutic stimulation to the patient with the controller and at least two electrodes using the preferred stimulation parameters.

8. The method of claim 1, further comprising:
   the controller transmitting data indicating that the controller is receptive to receiving data indicative of feedback; and
   receiving, at the patient input device, data indicative of the controller being receptive to receiving feedback.

9. The method of claim 1, further comprising:
   indicating, at the patient input device, with any one or more of a visual, vibrational or acoustic indication that the controller is receptive to receiving feedback.

10. The method of claim 1, further comprising the implanted controller storing values of the at least one stimulation parameter, and adjusting the at least one stimulation parameter by extrapolating or interpolating from the stored values.

11. The method of claim 1, further comprising the implanted controller storing values of the at least one parameter, and providing therapeutic stimulation based on the preferred set of parameters; wherein the stored parameters are associated with ratings and the preferred set of parameters is associated with a best rating.

12. The method of claim 11, wherein the ratings are numerical and the best rating comprises a rating with the highest or equal highest numerical value.

13. The method of claim 11, wherein the ratings comprise positive and negative ratings and the best rating comprises a rating with the most positive ratings.

14. The method of claim 1, wherein the machine learning algorithm applies a weighting to achieve any one or more of maximising battery lifetime, minimising side-effects, or minimising application of stimulation that may be less safe.

15. A controller for semi-autonomously adjusting therapeutic stimulation, the controller comprising:

a receiver to receive data indicative of feedback from the patient via a patient input device, wherein the feedback is associated with a patient rating of the therapeutic stimulation; and a processor configured to:
  generate a stimulation signal based on a plurality of stimulation parameters to be applied to the at least two implantable electrodes,
  automatically adjust at least one of the plurality of stimulation parameters within a respective limit without receiving more data from the patient via the patient input device, wherein the automatic adjusting of the at least one parameter includes a random adjustment of the at least one stimulation parameter being adjusted, and
  execute a machine learning algorithm based on the stimulation parameters and received data indicative of feedback, to determine preferred stimulation parameters; and wherein the controller is implantable into a patient, and connectable to at least two implantable electrodes.

16. The controller of claim 15, further configured to automatically adjust the at least one of the stimulation parameters to improve efficacy of the therapeutic stimulation based on the received data indicative of feedback from the patient.

17. The controller of claim 15, further comprising a storage medium capable of storing the plurality of stimulation parameters including the preferred stimulation parameters.

18. The controller of claim 15, further configured to repeatedly receive the data indicative of feedback and repeatedly adjust and generate the therapeutic stimulation signal to provide additional input for the machine learning.

19. The controller of claim 18, wherein the adjusting is repeated at regular time intervals.

20. The controller of claim 15, further comprising a transmitter to transmit data indicating that the controller is receptive to feedback from the patient.

21. A therapeutic stimulation system comprising:
  a controller according to claim 15; and
  a patient input device adapted to:
    receive feedback from the patient; and
    transmit the data indicative of feedback to the controller.

* * * * *